United States Patent [19]
Uesugi et al.

[11] Patent Number: 5,870,189
[45] Date of Patent: Feb. 9, 1999

[54] PARTICLE MONITOR AND PARTICLE-FREE RECESSING SYSTEM WITH PARTICLE MONITOR

[75] Inventors: Fumihiko Uesugi; Natsuko Ito, both of Tokyo, Japan

[73] Assignee: NEC Corporation, Tokyo, Japan

[21] Appl. No.: 837,942

[22] Filed: Apr. 28, 1997

[30] Foreign Application Priority Data

Apr. 26, 1996 [JP] Japan .................................... 8-130957
Oct. 25, 1996 [JP] Japan .................................... 8-301361

[51] Int. Cl.$^6$ .......................... G01N 15/02; G01N 21/00; G01J 4/00
[52] U.S. Cl. .......................... 356/335; 356/237; 356/370; 356/343; 250/559.39; 250/559.45
[58] Field of Search .................................... 356/237, 394, 356/366–367, 364, 370, 335–343; 250/559.39, 559.4, 559.41, 559.45, 559.47, 225, 564, 573–74

[56] References Cited

U.S. PATENT DOCUMENTS

| | | | |
|---|---|---|---|
| 3,612,688 | 10/1971 | Liskowitz | 356/342 |
| 4,804,853 | 2/1989 | Borden et al. | 356/338 |
| 5,008,558 | 4/1991 | Koshinaka et al. | 356/431 |
| 5,255,089 | 10/1993 | Dybas et al. | 359/337 |
| 5,355,212 | 10/1994 | Wells et al. | 356/237 |
| 5,659,390 | 8/1997 | Danko | 356/237 |

*Primary Examiner*—Robert Kim
*Attorney, Agent, or Firm*—Young & Thompson

[57] ABSTRACT

A particle monitor includes a light source for transmitting a light into a space over a wafer in wafer processing equipment to irradiate particles floating above the wafer for causing a scattered light; a photo-detector for detecting the scattered light to generate output signals corresponding to the intensity of the scattered light; a signal intensity judgment device for receiving the output signals from the photo-detector and comparing the output signals with a predetermined reference value already set in the signal intensity judgment device so as to judge whether the intensity of the scattered light is higher or lower than the predetermined reference value; and a display for displaying the intensity of the scattered light and luminance and distribution in intensity thereof or displaying distributions in size and the number of particles.

9 Claims, 9 Drawing Sheets

PARTICLE MONITOR AND PARTICLE-FREE RECESSING SYSTEM WITH PARTICLE MONITOR

BACKGROUND OF THE INVENTION

The present invention relates to a particle monitor, and more particularly to a particle monitor for monitoring in-situ particles or precursors thereof existing in a space above a wafer to detect in real time a spatial distribution as well as to an apparatus for removal of the particles from the space above the wafer on the basis of information about a real time spatial distribution of the particles to prevent the particles from adhering to the wafer.

Crystal defects of semiconductor due to particles may affect the quality and reliability of microelectronics devices. Particulate contamination control is one of the most important and major factors on the yield of modern large scale integrated circuits and packaging fabrication lines. For these reasons, tests for particles are carried out after some processes. It is possible to irradiate a laser beam onto a chip adhered with particles to cause laser beam scattering from which particles are detected. It is also possible to detect differences in particle images between adjacent two chips.

As the large scale integrated circuit has been scaled down, the difference in level of the surface of the chip is larger than the particle size, for which reason it is difficult to detect particles.

In place of the tests after the processes, it is possible to measure particles in the apparatus.

In the Japanese laid-open patent publication No. 3-39635, it is disclosed to use the laser beam scattering for particle detection, wherein even if the particle size is not more than 0.07 micrometers, an accurate detection of particles is possible. The particle detector is provided with the following elements. A light source is provided for emitting a laser beam. A flow cell is provided on an optical axis of the laser beam wherein a measured fluid flows through the flow cell. A pair of photo-detectors are provided on the optical axis of the laser beam and at opposite sides of the flow cell. A detector section is provided which are respectively connected to the photo-detectors. The detector section further has the following elements. Two recognition circuits are provided to be connected to the photo-detectors for detecting output signals from the photo-detectors to recognize output signals which exceed a predetermined threshold value. A judging circuit is provided which is connected to the two recognition circuits for fetching the output signals that exceed the predetermined threshold value from the recognition circuits to select only synchronous output signals and generate an output signal when a pair of the synchronous output signals could be detected. A counter circuit is also provided which is connected to the judging circuit for receiving the output signals from the judging circuit to count up the received output signals.

In the Japanese laid-open patent publication No. 4-52077, and Japanese laid-open utility model publication No. 3-39721, it is disclosed to use a technique wherein scattered lights are converted into electrical signals for display. This technique is also disclosed, for example, by Gary S. Selwyn in J. Vac. Sci. Technol. B9(6), November/December 1991, pp. 3487–3492 or by Y. Watanabe et al. in Appl. Phys. Lett. 61(13), 28 Sep. 1992, pp. 1510–1512.

Further, there is another technique wherein a polarized laser beam is irradiated toward particles to cause polarized laser beam scattering and variations in polarization between the incident laser beam and the scattered laser beam are measured. A laser beam emitted from a laser oscillator is then transmitted through a polarizer so that the laser beam is linearly polarized at an azimuth angle of 45 degrees from a horizontal plane. The polarized laser beam is transmitted into the processing equipment. The polarized laser beam is then scattered by particles in the processing equipment. The scattered polarized laser beam is then transmitted through a rotational analyzer into a photo-detector for obtaining output signals from the photo-detector. The intensity of the output signals from the photo-detector are measured in two cases when a quarter wavelength plate is provided in front of the photo-detector and when no quarter wavelength plate is provided in front of the photo-detector. As a result of the measurement of the intensity, it is possible to obtain signals modified at a rotation frequency of the rotational analyzer and varying over time. The modified signals are subjected to Fourier transformation to obtain Stokes parameters which are necessary to decide compositions of particles, number density and spatial distribution. This technique is disclosed for example by Hayashi et al. in Jap. J. Appl. Phys. Vol. 33 (1994) pp. L476–L478.

The first conventional technique disclosed in the Japanese laid-open patent publication No. 3-39635 is directed to an apparatus for measurement of particles in the fluid such as liquid and gaseous fluids by use of the laser beam scattering, wherein the measurement is made by introducing the measured fluid into the flow cell, for which reason it is difficult to take an interrelationship with particles into account.

The second conventional technique disclosed in the Japanese laid-open patent publication No. 4-352077 is directed to the conversion of the scattered light into image signals, wherein the image obtained when any smoke or dust is emitted is compared with another image obtained when no smoke or dust is emitted, so as to obtain a difference between the image so that it is possible to confirm emission of any smoke or any dust, but impossible to measure the density and the size of the smoke or the dust as well as distributions thereof. This means it difficult to find the mechanism for emission of the smoke or dust.

Also in the above conventional technique disclosed in the Japanese laid-open utility model publication No. 3-39721, the scattered light is collect by a photo-detector so that a plurality of laser emission diodes aligned display the size of particles and so that concentrations of particles are printed out by a printing machine. It is, however, difficult to find the mechanism for emission of particles which affect the yield of the wafer.

The other conventional technique disclosed by Gary S. Selwyn and by Watanabe is directed to measurement of particles in the space above the wafer in the processing equipment by use of the scattered light so that the scattered light is measured by a charge coupled device camera to obtain images of the scattered light. The obtained images are two-dimensional images wherein the scattered light from final particles of a small size of about several tens nanometers is not distinguishable from the scattered light from large size particles of the sub-micron or micron order sizes. The particles are in whole observed and imaged as a shining cloud, for which reason the obtained images are stored in a videotape recorder for subsequent calculations of the spatial distribution in size or diameter of the particles based upon the luminance. For these reasons, it is impossible to make a real-time measurement of the spatial distribution of the size of the particles. This means it difficult to follow rapidly variable states of the processing equipment. Namely, it is difficult to prevent wafer loss.

In order to measure the size and the density of the particles, the scattered light from a point in the space is measured. It is however impossible to measure all the movements and variations over time of the particles. This means it difficult to follow rapidly variable states of the processing equipment. Namely, it is difficult to prevent wafer loss.

The other conventional technique disclosed by Hayashi et al. uses the rotational analyzer for polarization analyze of the scattered light, wherein the measurements have to be made in both cases when the quarter wavelength plate is inserted on the optical axis and when no quarter wavelength plate is inserted thereon to obtain Stokes parameters necessary for presumptions of the diameters of the particles and number density thereof as well as refractive index.

At the present, single wafer processing equipment has been the main equipment for LSI manufacturing processes. Normally, it takes about 60–120 seconds to process a single wafer, for which reason it is necessary to do a continuous monitoring of generation of particles and provide in real-time the monitoring results to process engineers. Notwithstanding, the time of processing the single wafer, for example, about 60–120 seconds are too short for the rotational analyzing method to conduct continuous monitoring and real-time report to the process engineers because the rotational analyzing method is carried out by conducting two measurements in both cases when the quarter wavelength plate is inserted on the optical axis and when no quarter wavelength plate is inserted thereon to obtain Stokes parameters necessary for presumptions of the diameters of the particles and number density thereof as well as refractive index.

In the above circumstances, it had been required to develop a novel particle monitor for monitoring in-situ particles or precursors thereof existing in a space above a wafer to detect in real time a spatial distribution of particles as well as an apparatus for removal of the particles from the space above the wafer on the basis of information about a real time spatial distribution of the particles to prevent the particles from adhering to the wafer.

SUMMARY OF THE INVENTION

Accordingly, it is an object of the present invention to provide a particle monitor for monitoring in-situ particles or precursors thereof existing in a space above a wafer to detect in real time a spatial distribution of particles.

It is a further object of the present invention to provide an apparatus for removal of the particles from the space above the wafer on the basis of information about a real-time spatial distribution of the particles to prevent the particles from adhering to the wafer.

The present invention provides a particle monitor comprising a light source for emitting a light; a transmitter for transmitting the light into a space having particles above a wafer in wafer processing equipment to irradiate the light onto the particles for causing a scattered light; a photo-detector for detecting the scattered light or luminance to generate output signals corresponding to the intensity of the scattered light; a signal intensity judgment device for receiving the output signals from the photo-detector and comparing the output signals to a predetermined reference value already set in the signal intensity judgment device so as to judge whether the intensity of the scattered light is higher or lower than the predetermined reference value; and a display for displaying intensity of the scattered light and luminance and the distribution in density thereof, and/or displaying distributions in size and the number of particles.

It is preferable further to comprise a fixed optical analyzer and a rotatable wavelength plate for detecting variations in polarization of the scattered lights to find in real-time Stokes parameters variable over time which are necessary for presumptions of refractive indices of particles, and the size and distribution of the particles as well as numerical density of the particles.

It is preferable further to comprise a rotating device for rotating the wavelength plate.

It is preferable that the light source emits a pulse laser beam for counting the number of pulses of the pulse laser beam so that the wavelength plate is rotated every predetermined number of the pulses.

It is preferable further to comprise a controller for controlling operation of the wafer processing system on the basis of the output signals of the signal intensity judgment circuit.

It is preferable further to comprise an in-situ cleaner operable under the control of the controller.

It is preferable further to comprise a processing stopper device operable under controls by the above controller for stopping operation of the wafer processing for overhaul of the wafer processing equipment.

The present invention provides a particle monitor comprising a light source for emitting a light; a transmitter for transmitting the light into a space having particles above a wafer in wafer processing equipment to irradiate the light onto the particles for causing a scattered light; a fixed optical analyzer and a rotatable wavelength plate for detecting variations in polarization of the scattered light to find in real-time Stokes parameters variable over time which are necessary for presumptions of refractive indices of particles, and the size and distribution of the particles as well as numerical density of the particles; a photo-detector for detecting the scattered light or luminance to generate output signals corresponding to the intensity of the scattered light; a signal intensity judgment device for receiving the output signals from the photo-detector and comparing the output signals to a predetermined reference value already set in the signal intensity judgment device so as to judge whether the intensity of the scattered light is higher or lower than the predetermined reference value; and a display for displaying the intensity of the scattered light and luminance and distributions in intensity thereof, and/or displaying distributions in size and the number of particles.

It is preferable that the light source emits a pulse laser beam for counting the number of pulses of the pulse laser beam so that the wavelength plate is rotated ever predetermined number of the pulses.

It is preferable further to comprise a controller for controlling operation of the wafer processing equipment on the basis of the output signals of the signal intensity judgment circuit.

It is preferable further to comprise an in-situ cleaner operable under the control of the controller.

It is preferable further to comprise a processing stopper device operable under control of the controller for stopping operation of the wafer processing for overhaul of the wafer processing equipment.

BRIEF DESCRIPTIONS OF THE DRAWINGS

Preferred embodiments of the present invention will be described in detail with reference to the accompanying drawings.

Figure 15:
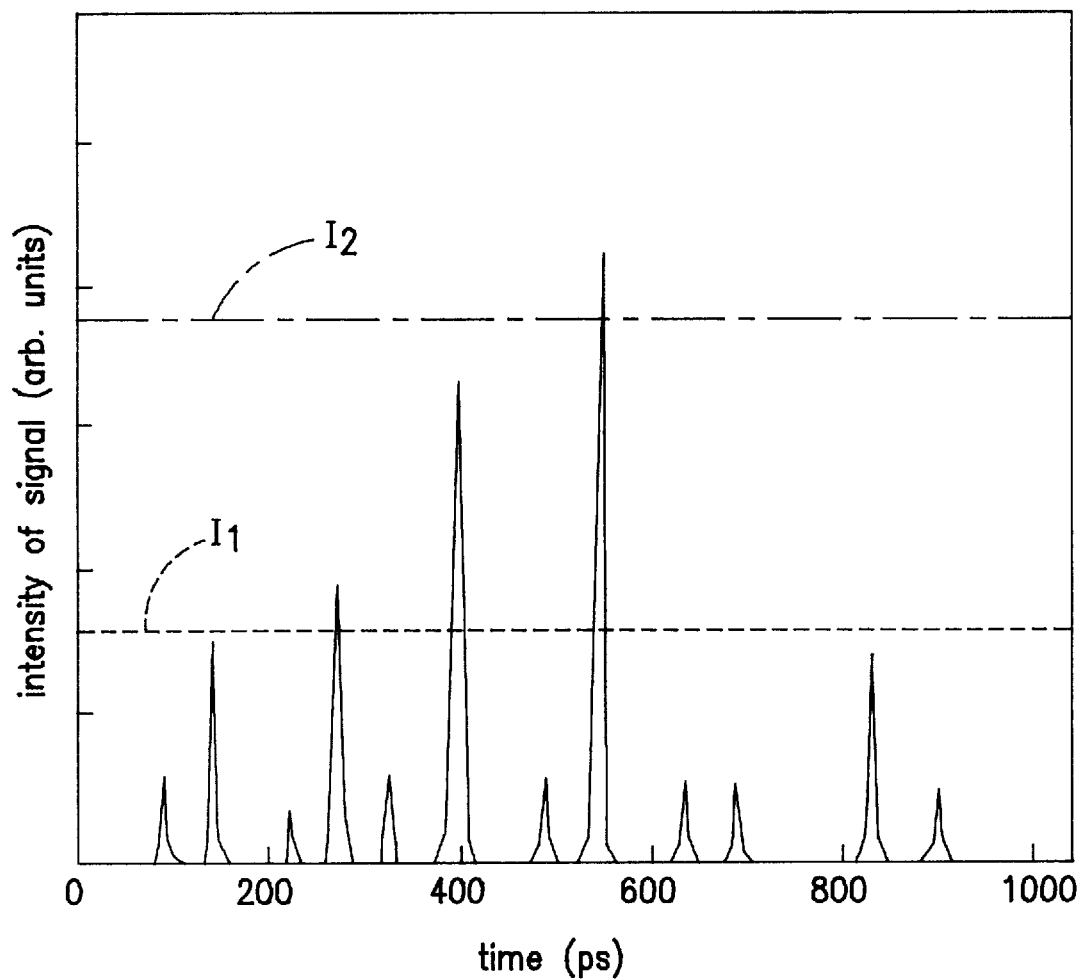

FIG. 15 its a diagram illustrative of variations in intensity of scattered light versus time.

DISCLOSURE OF THE INVENTION

In accordance with the present invention, a novel particle monitor comprises a light source for emitting a light, a transmitter for transmitting the light into a space having particles above a wafer in wafer processing equipment to irradiate the light onto the particles for causing a scattered light, a photo-detector for detecting the scattered light or luminance to generate output signals corresponding to the intensity of the scattered light, a signal intensity judgment circuit for receiving the output signals from the photo-detector and comparing the output signals with a predetermined reference value to judge whether the intensity of the scattered light is higher or lower than the predetermined reference value, and a display for displaying intensity of the scattered light and luminance and distribution in intensity thereof and/or displaying distributions in size and the number of particles.

The particle monitor according to the present invention uses an optical analyzer and a wavelength plate for detecting variations in polarization of the scattered light. The particle monitor further has a rotating mechanism for rotating the wavelength plate to find in real-time Stokes parameters variable over time which are necessary for presumptions of refractive index of particles, and size and distribution of the particles as well as numerical density of the particles.

The particle monitor uses a pulse laser beam for counting the number of pulses of the pulse laser beam so that the wavelength plate is rotated every predetermined number of the pulses.

It is possible that a controller is provided for controlling operations of the wafer processing equipment on the basis of the output signals of the signal intensity judgment circuit.

It is also possible to provide the wafer processing equipment with an in-situ cleaner which is operable under the control of the above controller.

It is also possible to provide the wafer processing equipment with a processing stopper device for stopping the operations of the wafer processing equipment for overhaul of the wafer processing equipment, wherein the processing stopper device is operable under control of the above controller.

The above present invention will be described in more detail with reference to the accompanying drawings.

In order to reduce the defects due to the particles generated in the processes and improve circuit performance, reliability and yield, it is necessary to detect particles of a few nanometers to several tens nanometers in size. For this purpose, normally visible rays of light are used for providing no influence to any reaction in the processes.

The objective particles have a size which is smaller in digit order than the wavelength of the visible light to be used. The main scattering is Rayleigh scattering. The intensity I of the light with a wavelength $\lambda$ which has been Rayleigh-scattered by particles having a radius of "a", a double refractive index "m" and the numerical density of N is given by the following equation.

$$I = A(2\pi/\lambda)^4 f(m) a^6 N I_0 \qquad (1)$$

where $A=(1+\cos^2\theta)/2r^2$, and $$f(m)=|(m^2-1)/(m^2+2)|^2$$

where $I_0$ is the intensity of the incident light, r is the distance between scatterer and the measuring point and $\theta$ is the angle between a traveling direction of the laser beam and a direction from the scatterer to the measuring point.

When the photo-detector receives the scattered light, the intensity S of the received signal is given by the following equation.

$$S=\eta I \qquad (2)$$

where $\eta$ is the efficiency of conversion into electrical signals.

Figure 3:
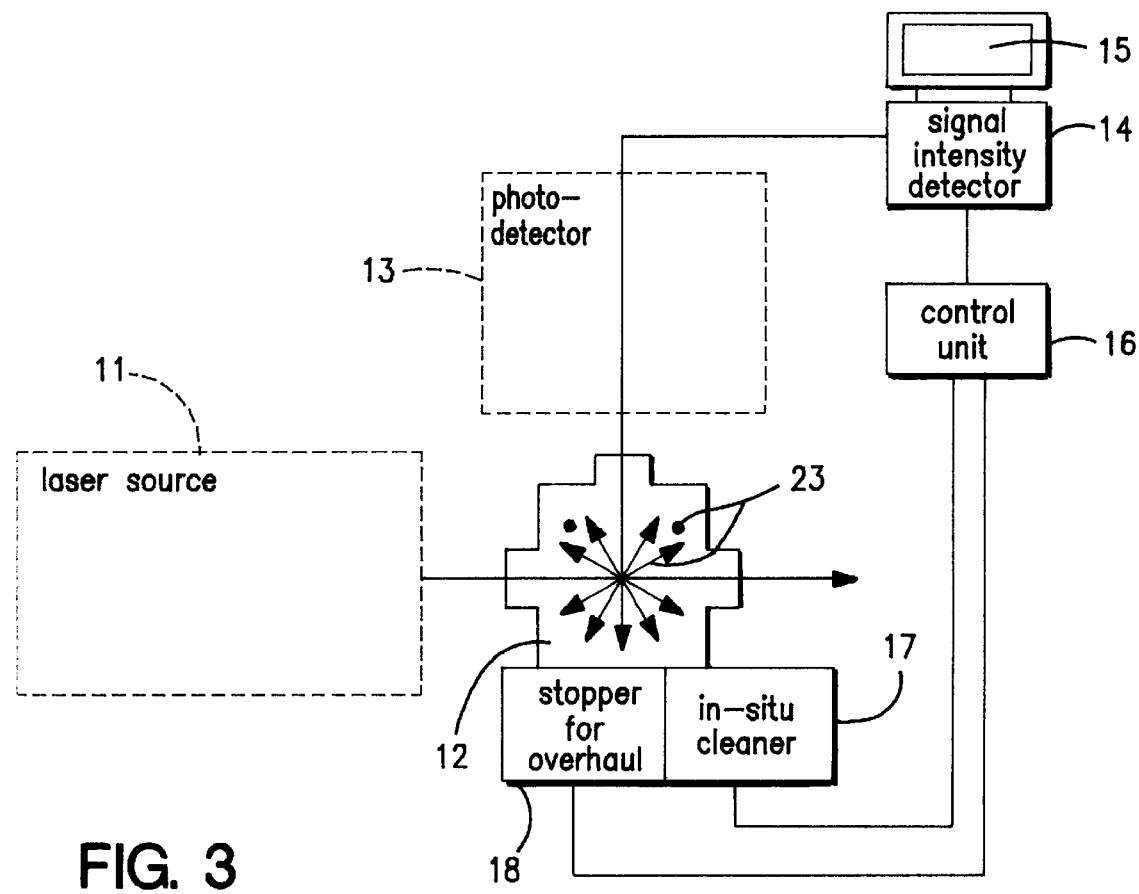
FIG. 3 is a schematic view illustrative of a structure of a particle monitor in accordance with the present invention.
Figure 5:
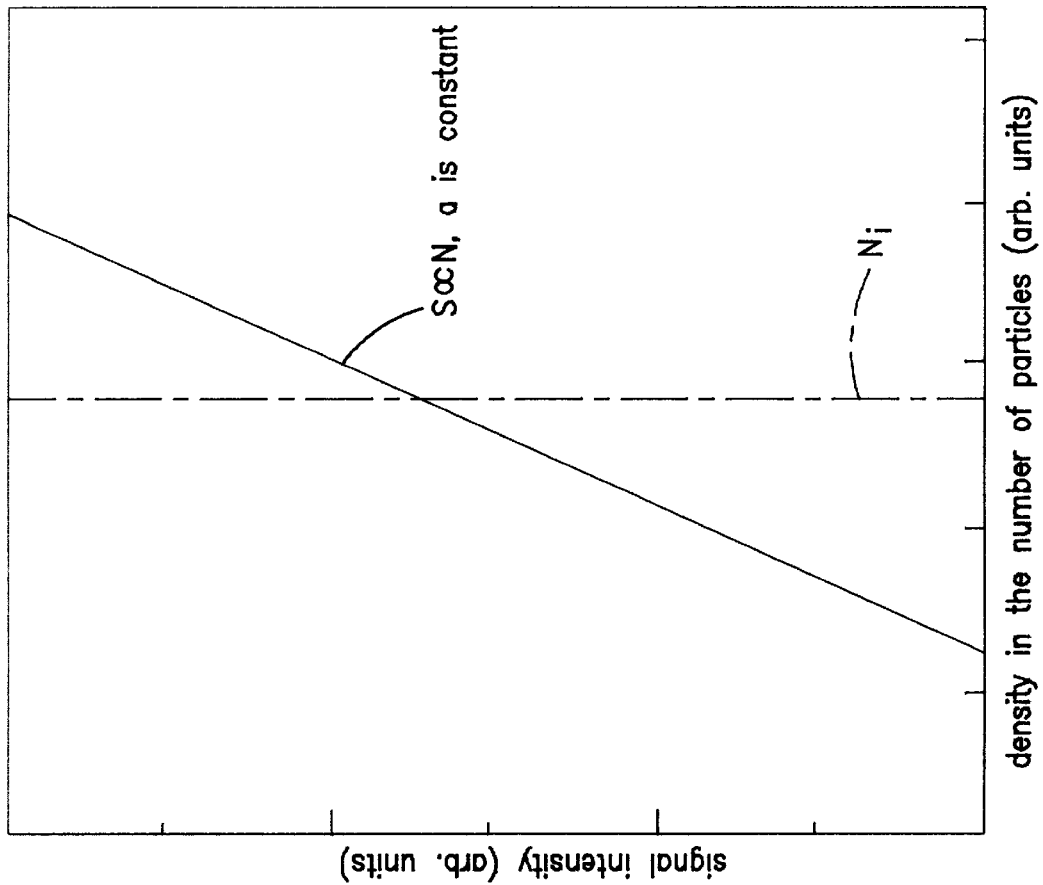
FIG. 5 is a diagram illustrative of variations in intensity of scattered light versus particle number density.
Figure 4:
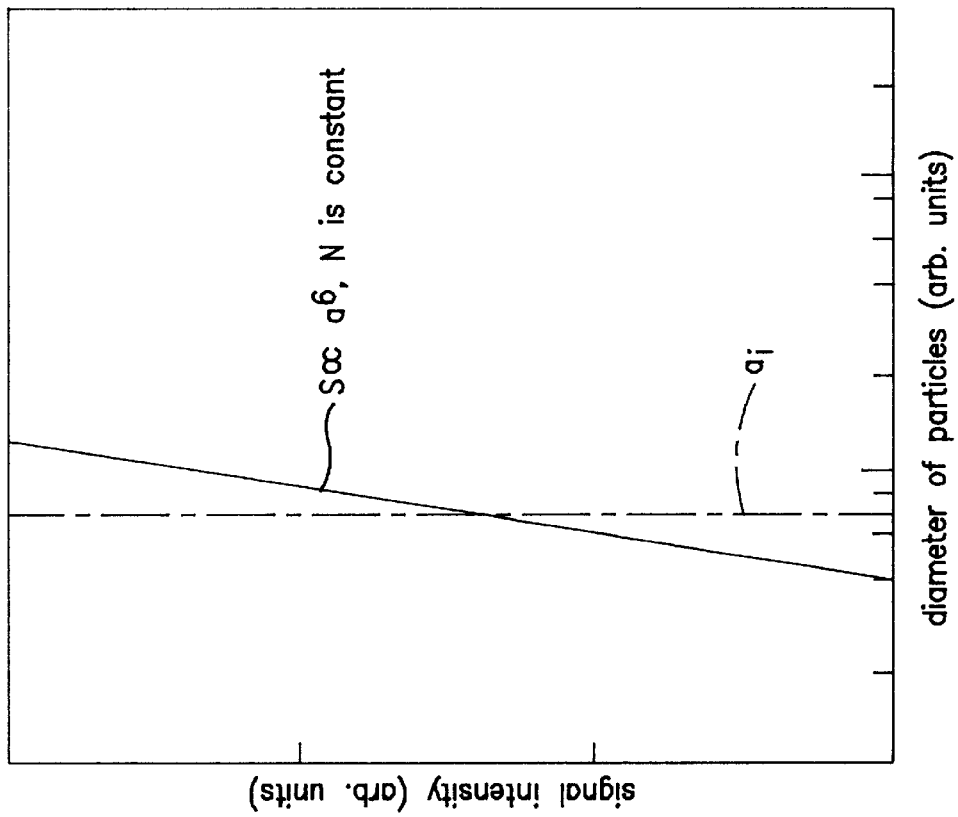
FIG. 4 is a diagram illustrative of variations in intensity of scattered light versus particle diameter.
Figure 6:
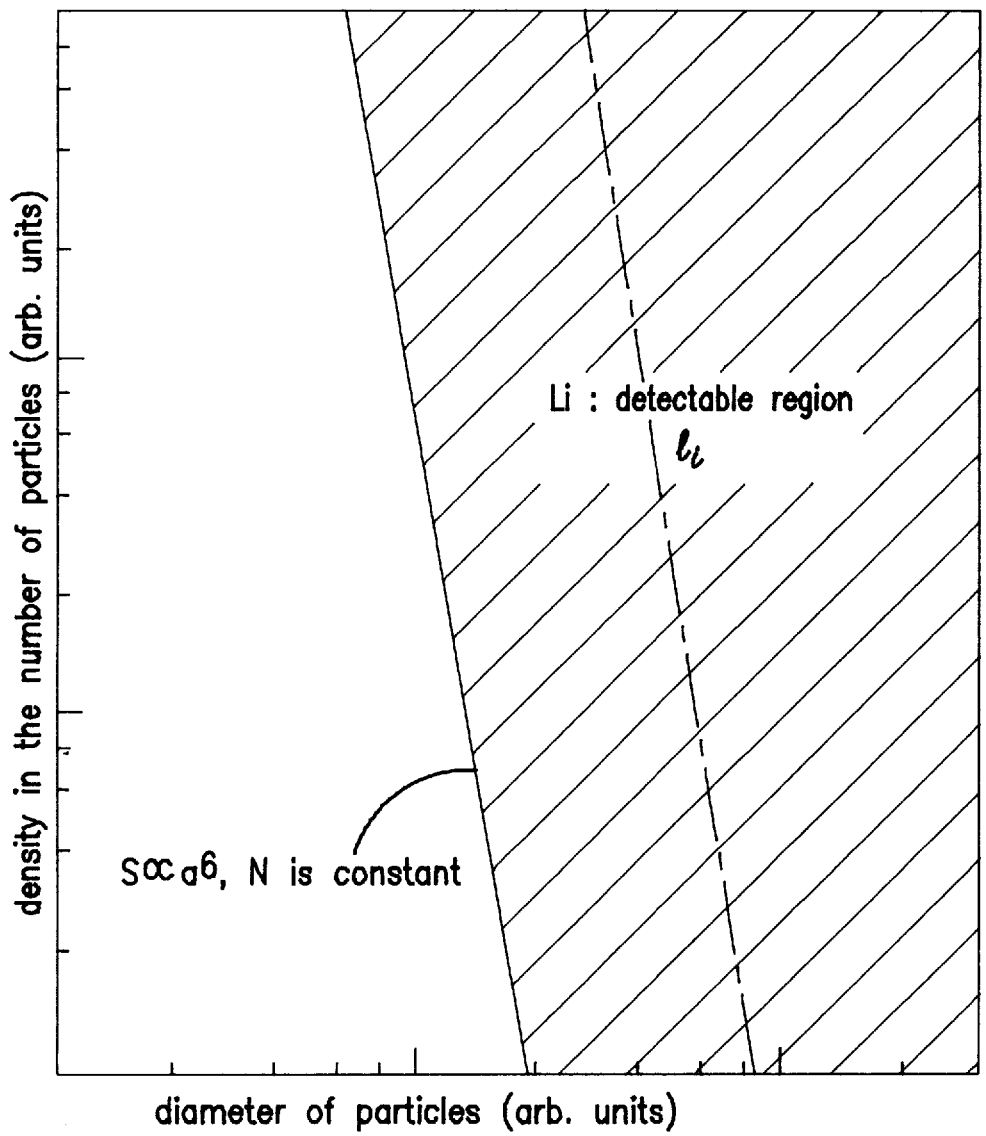
FIG. 6 is a diagram illustrative of variations in particle number density versus particle diameter.

When, as illustrated in FIG. 3, the scattered light from the particles in processing equipment 12 is observed in a direction perpendicular to an incident light and the scattered light is received by a photo-detector comprising CCD arrays, variations in intensity of the output signal from the photo-detector versus particle diameter are as illustrated in FIG. 4 whilst variations in intensity of the output signal from the photo-detector versus numerical density are as illustrated in FIG. 5. From those results illustrated in FIGS. 4 and 5, a relationship of diameter of the detectable particles to numerical density thereof is obtained as illustrated in FIG. 6.

In order to presume formations of defects due to particles ono the wafer, it is necessary to detect in-situ fine particles having such small size and numerical density as having a potential but not existent capability of causing the defects to monitor growth process of the particles.

Variations in size and numerical density of the particles are monitored to give the process engineer a notice when either the sizes or density exceed the reference values or to control automatically the operations of the wafer processing equipment to suppress generation of further particles. Alternatively, it is also preferable to do in-situ cleaning by the in-situ cleaner or send the wafer processing equipment for overhaul. In FIG. 4, "$a_i$" represents the reference value in size of the particles and in FIG. 5, "$N_i$" represents the reference value in number density of the particles. In FIG. 6, straight line "$l_i$" is obtained from the relationship of "$a_i$" and "$N_i$".

"$a_i$", "$N_i$" and "$l_i$" depend upon the kinds and materials of the process and processing equipment as well as degree of integration of the LSI to be fabricated. If requirements are not simple judgment of continuing or discontinuing the operations of the processing equipment but complicated judgments of warning in generation of fine and immature particles, and warning of mature particles having been grown that are capable of causing defects as well as issuance of instruction for cleaning or overhaul, then "$a_i$", "$N_i$" and "$l_i$" have to be set as reference values for judgments.

The incident laser for causing the scattering may be either a continuous laser beam or a pulse laser beam. Notwithstanding, the pulse laser beam has the following advantages. In observations of back scattering or forward scattering, the scattering intensity given by the equation (1) provides the size of the particles.

With reference to incident time of an incident laser pulse, the number of existent particles is obtained from the number of pulses of the scattered light observed. This means it possible to measure the size and the number of the particles separately.

Figure 1:
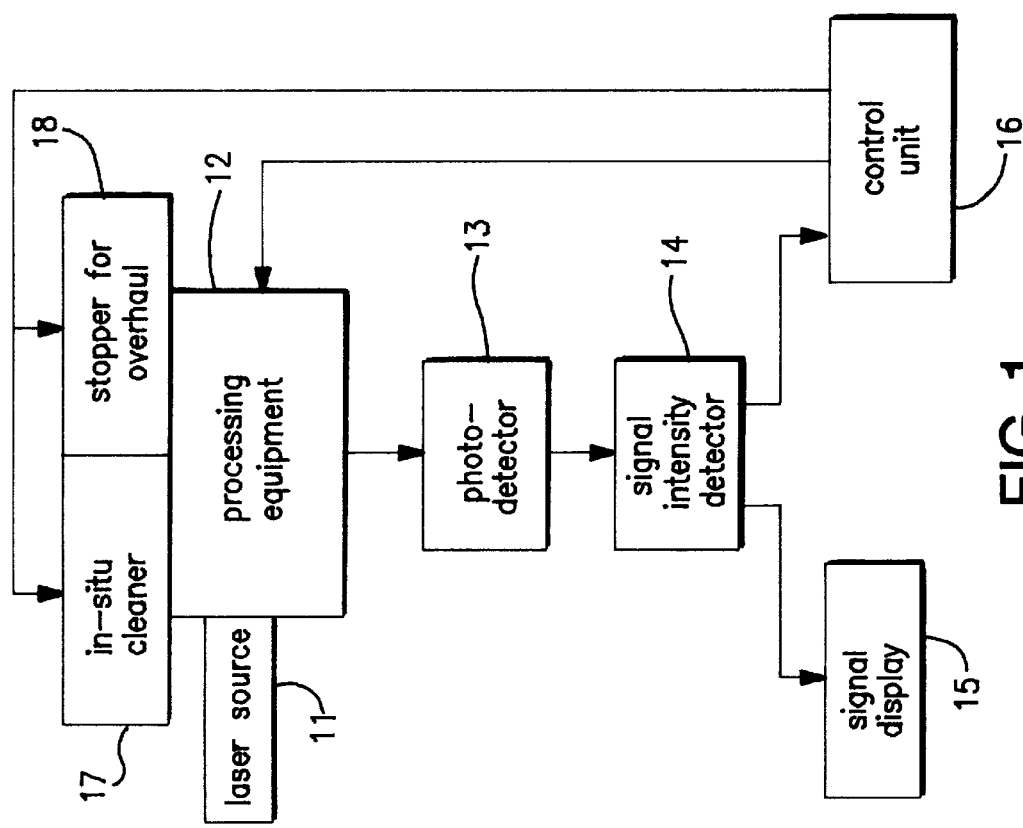
FIG. 1 is a block diagram illustrative of a structure of a particle monitor in accordance with the present invention.

FIG. 1 is a block diagram illustrative of a particle monitor and a wafer processing equipment. A laser source 11 is provided which comprises a laser oscillator for emitting a laser beam and a laser scanner for a spatial scanning of the emitted laser beam. The scanning laser beam is introduced into wafer processing equipment 12 and scattered by particles floating in the processing equipment 12. The laser beam may be either Rayleigh-scattered to have the same wavelength as that of the incident laser beam or Raman-scattered to have a different wavelength from the wavelength of the incident laser beam. The main scattering may be the Rayleigh-scattering, but depending upon a material, Raman-scattering may be caused or luminescence may be caused.

The scattered light is received by a photo-detector and converted into electrical signals. Whereas it is preferable that the signal intensity is linearly proportional to the intensity of the scattered light, it is also possible that the signal intensity has one-to-one correspondence to the intensity of the scattered light even which is non-liner.

As the photo-detector 13, any photo-electric converters such as a charge coupled device, a photo-multiplier, a multichannelplier are available. It is also possible to provide a monochromator in front of the photo-detector 13. When Raman-scattered light or luminescence is observed, the use of the monochromator is effective for isolation thereof from the incident laser beam and from light in the atmosphere.

The electrical signals from the photo-detector 13 are input to a signal intensity judging device 14 in which a reference intensity Ii has been set which corresponds to the values "$a_i$", "$N_i$" and "$l_i$", to judge whether the intensity I of the signal is larger or smaller than the reference intensity $I_i$. If the intensity I of the signal is smaller than the reference intensity $I_i$, the display for continuing the processes is made. If, however, the intensity I of the signal is equal to or larger than the reference intensity $I_i$, the display for in-situ cleaning or overhaul is made.

A display also displays variations of the signal intensity I over time, approaching of the signal intensity I to the reference intensity $I_i$ and spatial distribution of the signal intensity I in the processor to allow the process engineer to know the states of the processing equipment or the processes.

Also, the signal from the signal intensity judging device 14 is also transmitted to a controller 16. The controller 16 makes feed-back controls to the processing equipment 12 in accordance with the result of the judgment to keep the processing equipment 12 in optimal condition.

If a slight amount of particles is generated even under I<$I_i$, the controller detects variations in power, temperature, and gas flow rate and the like and controls them to keep the optimal conditions.

If, I≧$I_i$, the controller 16 instructs the in-situ cleaner 17 to make the in-situ cleaning or instructs the processing equipment 12 to discontinue the current operations for overhaul. If there are a plurality of the reference intensity values, precise display and control are possible.

The in-situ and real-time monitoring of the processing equipment and presumptions thereof are made on the basis of the measurement results of the scattered light scattered by the particles. On the basis of the above equation (1), the reference value to radius "a" and the reference value to numerical density "N" are determined to find the reference intensity of the scattered light for comparison of the actually measured intensity of the scattered light to the reference intensity.

It is preferable that the double refractive index "m" is presumable separately, the spatial distributions can be obtained for every particle components. As a result, the accuracy of presumptions is considerably improved.

In order to presume "a", "N" and "m" independently, a polarized laser beam is introduced into the processor to measure variations of the polarization of the scattered light with reference to the polarization of the incident light.

Figure 7:
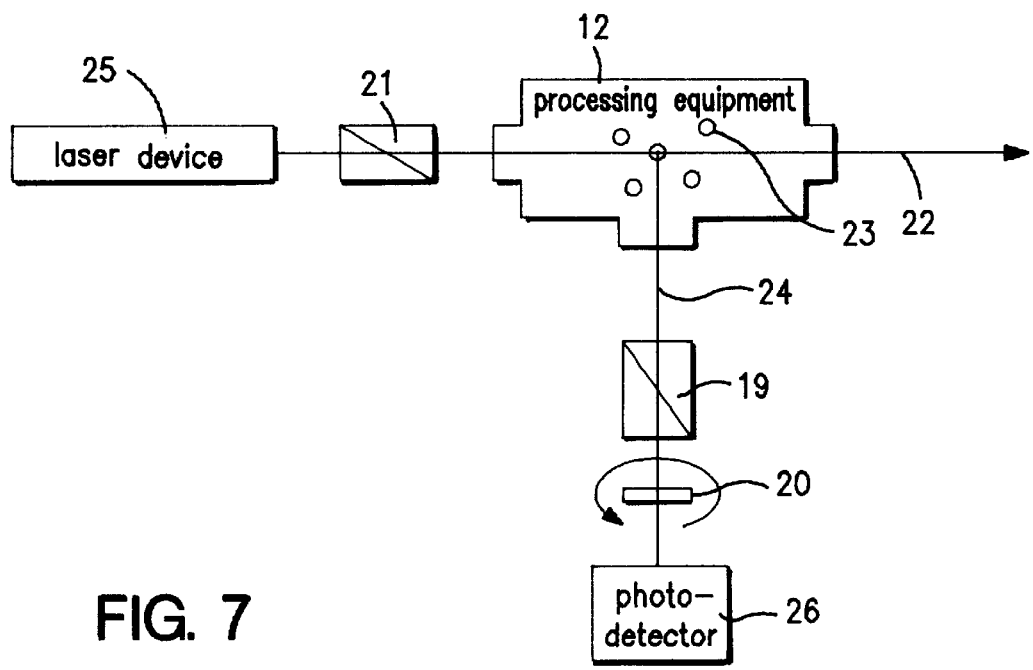
FIG. 7 is a schematic view illustrative of another structure of a particle monitor in accordance with the present invention.

The method of analyzing the polarization of the scattered light is disclosed in the Jpn. J. Appl. Phys. Vol. 33, 1994, pp. L476–L478. The structure of the particle monitor is illustrated in FIG. 7. The analyzer 19 is fixed. The wavelength plate is a rotational quarter wavelength plate 20.

The laser beam is polarized by the polarizer 21 and then introduced into the processing equipment 12. The polarized laser beam is scattered by the particles 23 in the processing equipment 12. The scattered laser beam 24 is then transmitted through the fixed analyzer 19 to the rotational quarter wavelength plate 20 before the scattered light is received by the photo-detector 26. The intensity I of the scattered light received by the photo-detector 26 is given by the following equation.

$$I = I_{dc}(2-Q) - I_{dc}Q \cos 4\omega t + I_{dc}2V \sin 2\omega t - I_{dc}U \sin 4\omega t$$

where $I_{dc}$ is the direct current component from the photo-detector 26, Q=−cos2 ψ, U=sin2 ψ cos Δ, V=−sin2 ψ sin Δ, tan ψ is the ratio in intensity of horizontal component to vertical component of the scattered light, Δ is the difference in phase of between horizontal and vertical components of the scattered light, and ω is the angular velocity of the rotation of the quarter wavelength plate.

Variations in intensity of the scattered light received by the photo-detector 26 over time include al of the Stokes parameters, for which reason the variations thereof over time is Fourier-transformed into Fourier coefficient of the rotational angular velocity of the quarter wavelength plate to find those Stokes parameters.

The conventional method disclosed in Jpn. J. Appl. Phys. Vol. 33, 1994, pp. L476–L478 require two measurements in cases of the use of the quarter wavelength plate and no use thereof to find "Q", "U", and "V". By contrast, in accordance with the present invention it is possible to find radii of particles and optical constants and numerical density by a single measurement. The requirement for but a single measurement means that it possible not only to monitor in-situ and in real-time particles, but also to presume a refractive index in-situ and in real-time.

By use of the method of rotation of the quarter wavelength plate, it is possible to distinguish whether the particles are grown by the reaction in the processes or generated by flaking from the electrodes or inner walls of the processor because the particles grown by the reaction differ in composition from the particles generated by flaking and this compositional difference between them appears as the difference in refractive index of the light.

The present invention permits real-time response to the cause of generation of the particles. Against the particles grown by the reaction and floating, it is effective to change the process conditions. By contrast, against the particles generated by flaking from the inner wall, it is effective to conduct the in-situ cleaning or overhaul.

Figure 2:
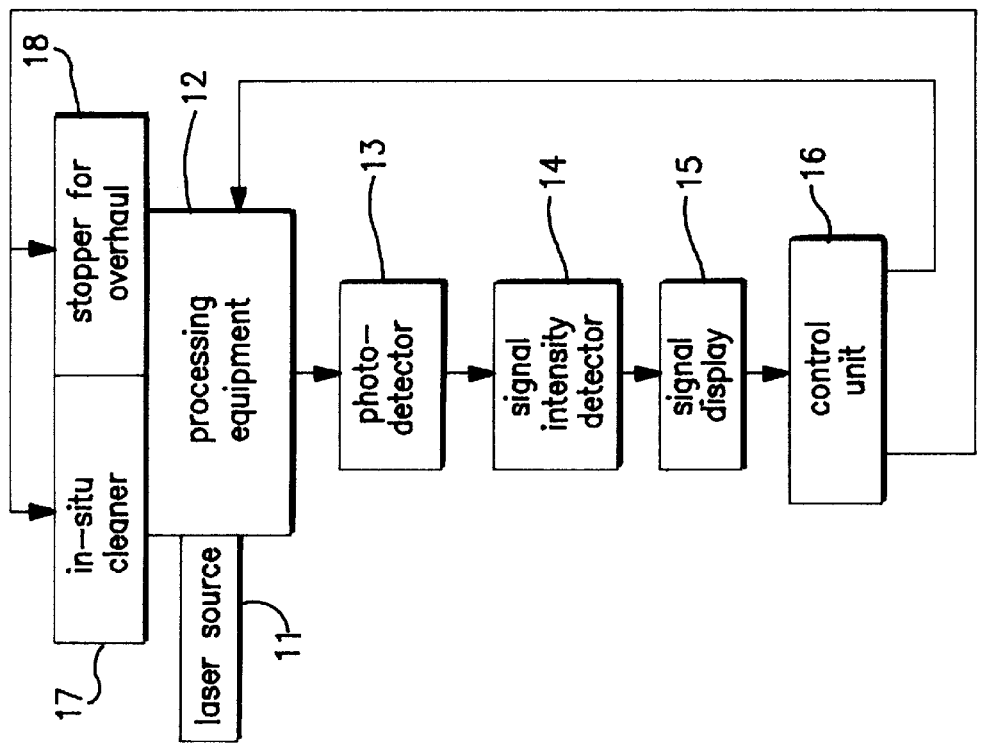
FIG. 2 is a block diagram illustrative of another structure of a particle monitor in accordance with the present invention.

In this embodiment, the signals are transmitted as illustrated in FIGS. 1 and 2 but "$a_i$", "$N_i$" and "$l_i$" may be determined for each refractive index "m".

The judgment for signal intensity may be made as described above.

As described above, the particles in the process may be detected by measuring the scattered light to compare the measured signal intensity with the reference intensity for monitoring the states in the processing equipment in-situ and in real-time.

FIRST EMBODIMENT

Figure 8:
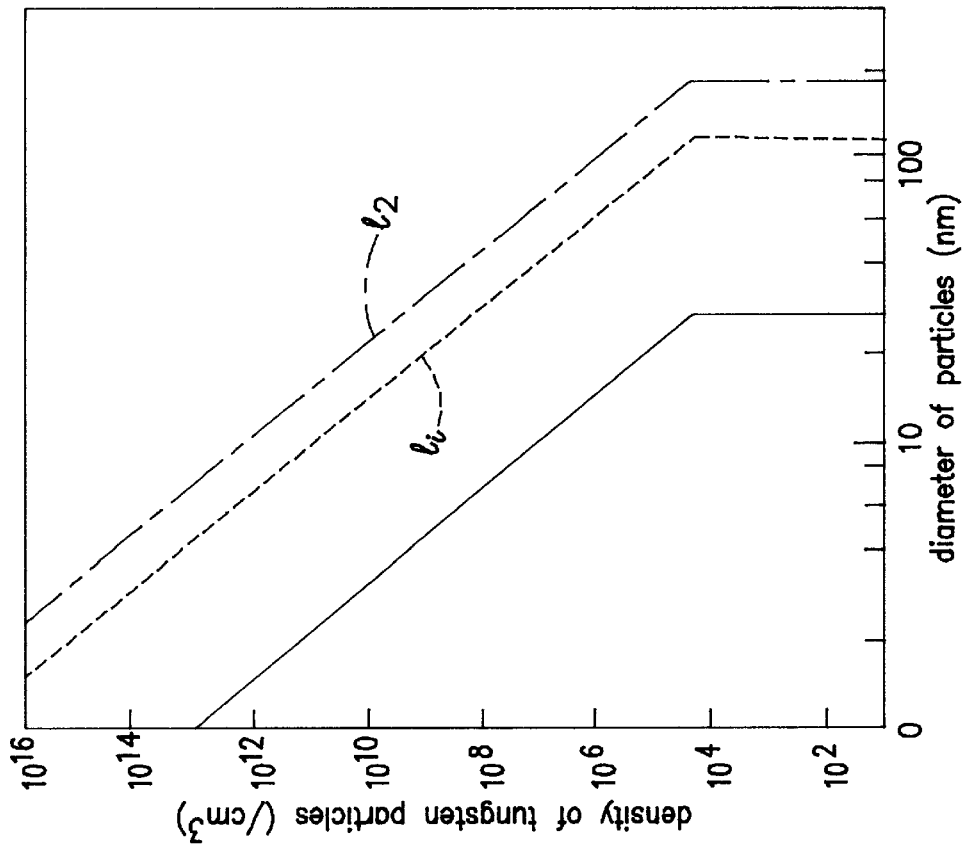
FIG. 8 is a diagram illustrative of variations in number density of tungsten particles versus particle diameter.

A first embodiment of the present invention will be described, in which a thermal CVD process is carried out by use of tungsten. FIG. 3 illustrates the structure of the particle monitor of this embodiment. FIG. 8 illustrates a relationship of signal intensity of the scattered light to particle diameter when a second harmonic generation wavelength of 532 nm obtained from a YAG laser is used.

The diameter of the particles is the factor to decide whether the feed-back control to the thermal CVD equipment is made or not. The diameter of the particles and number density are set so that $a_1=20$ nm, $a_2=$is 100 nm $N_1$ is $1\times10^9$ cm$^{-3}$, and $N_2$ is $1\times10^6$ cm$^{-3}$. The line $l_1$ is decided from $a_1$ and $N_1$ whilst the line $l_2$ is $a_2$ and $N_2$. The lines $l_1$ and $l_2$ are illustrated in FIG. 8.

If the intensity of the scattered light is smaller than $l_1$, then no particle has been generated.

If the intensity of the scattered light is larger than $l_1$ but smaller than $l_2$, then particles have been generated but no defect is caused due to the particles.

If the intensity of the scattered light is larger than $l_2$, then defects may be caused due to the particles.

The monitoring and feed-back operations will be described with reference to FIG. $l_1$ and $l_2$ have been set in the signal intensity judgment device 14.

If almost no particles have been generated, then almost no scattering of the light from the laser source 11 is caused. As a result, the intensity of the signal transmitted from the photo-detector 13 to the signal intensity judgment device 14 is small. In this case, the intensity of the signal is recognized to be smaller than $l_1$ and this signal is then transmitted to the display 14 for display. Also the signal is transmitted to the controller 16 but the controller does not feed-back to the processing equipment 12.

If the signal intensity is larger than $l_1$ but smaller than $l_2$, the signal is displayed by the display 15. At the same time, the controller 16 issues a stand-by instruction to the in-situ cleaner 17. After the treatment to the wafer in the processing equipment 12 has been finished, then the intended in-situ cleaning is carried out by use of $NF_3$ gas so that the processing equipment 12 is returned to the normal state.

If the signal intensity is larger than $l_2$, the signal is displayed by the display 15. At the same time, the controller 16 issues a stand-by instruction to the processing stopper 18 for external checking of the processing equipment 12. If no abnormal state is confirmed, then the processor will again start operations. If, however, any abnormal state is confirmed, then the overhaul of the processor is made.

The intensity of the scattered light is monitored for comparison to the reference value and from the result of the comparison the controller makes the feed-back to the processing equipment so as to reduce the down time of the processor and reduce the possibility of generation of the particles.

Whereas in this embodiment, the diameter of the particles and numerical density are set so that $a_1=20$ nm, $a_2=100$ nm $N_1$ is $1\times10^9$ cm$^{-3}$, and $N_2$ is $1\times10^6$ cm$^{-3}$, those values may be adopted to accord to the processor and processing conditions.

Further in this embodiment, the signal from the signal intensity judgment device 14 is transmitted to the display 15 and simultaneously to the controller 16. Notwithstanding, it is also possible that as illustrated in FIG. 2, the signal from the signal intensity judgment device 14 is transmitted through the display 15 to the controller 16. In this case, the process engineer reviews the display 15 to operate the controller 16.

In this embodiment, the laser beam is not spatially scanned. It is, however, possible to provide a scanner for scanning spatially laser beam for obtaining two-dimensional and three dimensional distributions of the intensity of the scattered light. Those distributions may be displayed in the display 15 to allow the process engineer to know the generation and distribution of the particles.

SECOND EMBODIMENT

Figure 9:
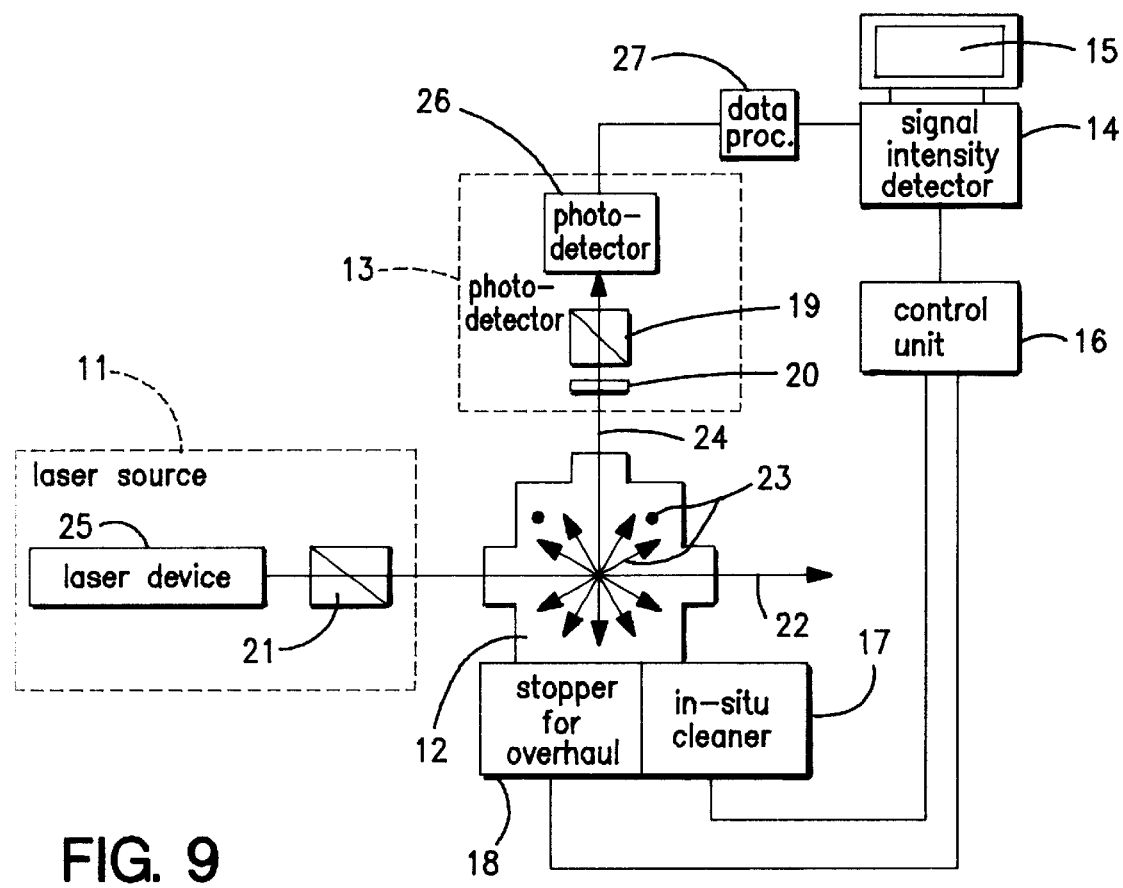
FIG. 9 is a schematic view illustrative of still another structure of a particle monitor in accordance with the present invention.

A second embodiment of the present invention will be described, in which a plasma etching process of tungsten is carried out. FIG. 9 illustrates the structure of the particle monitor of this embodiment. The laser source 11 includes a laser 25 including a YAG laser oscillator and a second harmonic generation non-linear optical crystal and also the laser source 11 includes a polarizer 21. The laser beam is transmitted through the polarizer 21 to be made into a linearly polarized laser beam 22 with 45 degrees polarization and a wavelength of 532 nm. the laser beam 22 is scattered by particle 23 floating in the processing equipment 12. The scattered light 24 is then transmitted through the rotational quarter wavelength plate 20 rotating at a constant rotation speed and a fixed analyzer 19 to the photo-detector 26 which is provided with an interference filter.

A data processor 27 executes the Fourier transformation of variations in the intensity of the scattered light over time to find the relationship of the equation (3) and further find the Stokes parameters Q, U, V. From the Stokes parameters Q, U, V, the parameters $\psi$, $\Delta$ are calculated to find the diameter of the particles and optical refractive index as well as numerical density of the particles.

Figure 10:
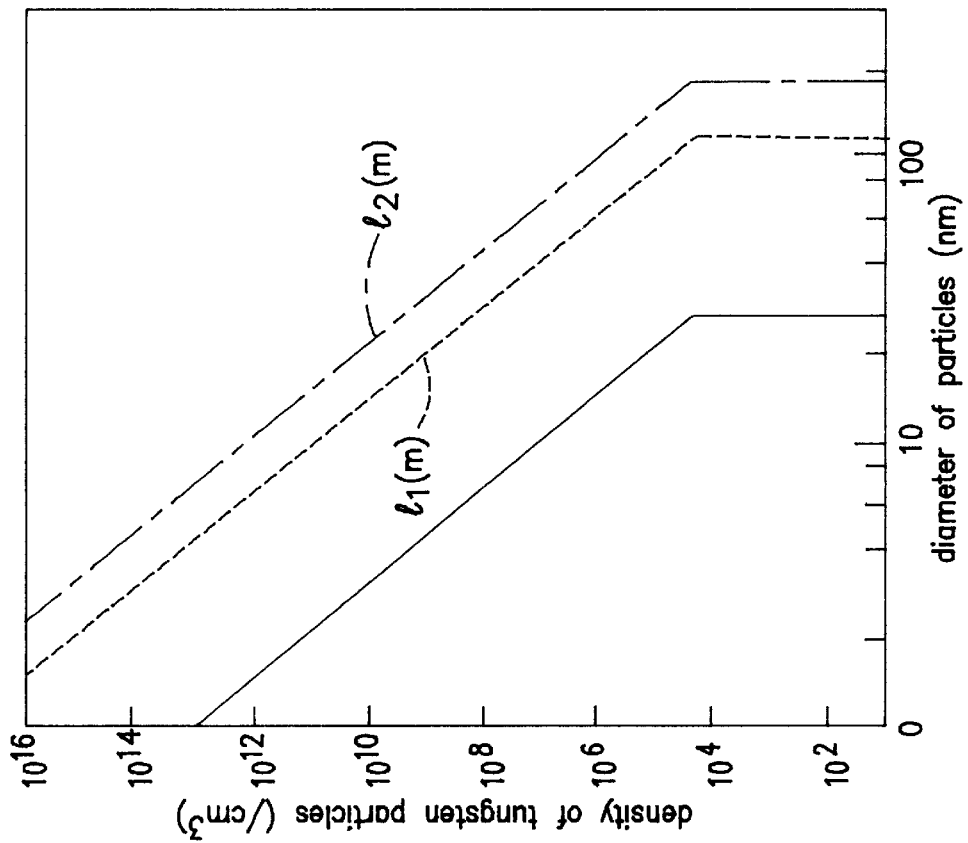
FIG. 10 is a diagram illustrative of variations in number density of tungsten particles versus particle diameter.

The diameter of the particles is the factor to decide whether the feed-back control to the etching system is made or not. The diameter of the particles and number density are set so that $a_1=20$ nm, $a_2=100$ nm $N_1$ is $1\times10^9$ cm$^{-3}$, and $N_2$ is $1\times10^6$ cm$^{-3}$. The refractive index "m" is calculated by the data processor 27. The line $l_1$ is decided from a1 and $N_1$ as well as "m", whilst the line $l_2$ is $a_2$ and $N_2$ as well as "m". The lines $l_1$ and $l_2$ are illustrated in FIG. 10.

The particles vary in diameter and in compositions at a center and a surface portion thereof during the growth process whereby the refractive index may be changed. In FIG. 10, the lines $l_1$ and $l_2$ may be changed. Since the data processor 27 calculate "m", "a" and "N", it is possible to judge the signal intensity is larger or smaller than $l_1$ or $l_2$.

If the intensity of the scattered light is smaller than $l_1$, then no particle has been generated.

If the intensity of the scattered light is larger than $l_1$ but smaller than $l_2$, then particles have been generated but no defect is caused due to the particles.

If the intensity of the scattered light is larger than $l_2$, then defects may be caused due to the particles.

Figure 11:
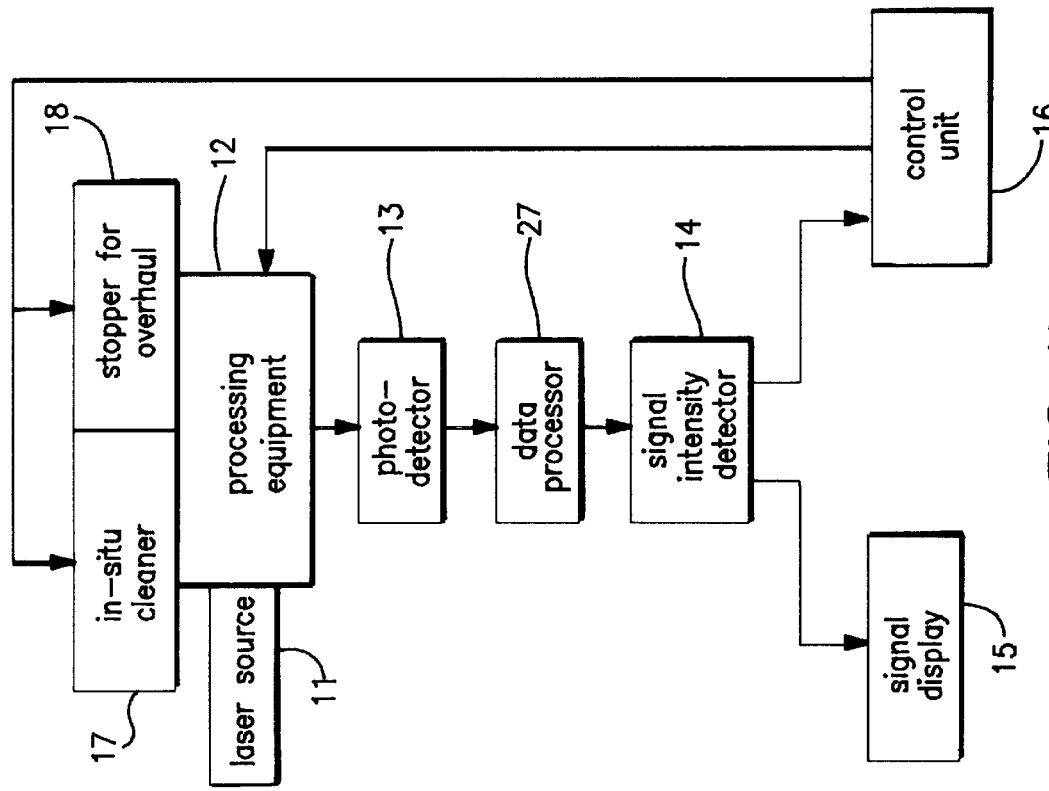
FIG. 11 is still another structure of a particle monitor in accordance with the present invention.

The monitoring and feed-back operations will be described with reference to FIG. 11. $l_1$ and $l_2$ have been set in the signal intensity judgment device 14.

The signals from the photo-detector 13 are input to the data processor 27 to calculate the radius "a" of the particles, the numerical density "N" and the refractive index "m".

Parameters "$a_1$", "$a_2$", "$N_1$" and "$N_2$" have previously been set in the signal intensity judgment device 14. To the refractive index "m", $l_1$ and $l_2$ are sequentially determined for comparisons thereof to the intensity of the scattered light determined from "a", "N" and "m" to judge whether the measured intensity is larger or smaller than the reference intensity.

If almost no particle has been generated, then almost no scattering of the light from the laser source 11 is caused. As a result, the intensity of the signal transmitted from the photo-detector 13 to the signal intensity judgment device 14 is small. In this case, the intensity of the signal is recognized to be smaller than $l_1$ and this signal is then transmitted to the display 14 for display. Also the signal is transmitted to the controller 16 but the controller does not feed-back to the processing equipment 12.

If the signal intensity is larger than $l_1$ but smaller than $l_2$, the signal is displayed by the display 15. At the same time, the controller 16 issues a stand-by instruction to the in-situ cleaner 17. After the treatment to the wafer in the processing equipment 12 has been finished, then the intended in-situ cleaning is carried out by use of $NF_3$ gas so that the processing equipment 12 is returned to the normal state.

If the signal intensity is larger than 12, the signal is displayed by the display 15. At the same time, the controller 16 issues a stand-by instruction to the processing stopper 18 for external checking of the processing equipment 12. If no abnormal state is confirmed, then the processing equipment will again start operations. If, however, any abnormal state is confirmed, then the overhaul of the processing equipment is made.

The intensity of the scattered light is monitored for comparison to the reference value and from the result of the comparison the controller makes the feed-back to the processing equipment so as to reduce the down time of the processing equipment and reduce the possibility of generation of the particles.

Whereas in this embodiment, the diameter of the particles and number density are set so that $a_1$=20 nm, $a_2$=100 nm $N_1$ is $1 \times 10^9$ cm$^{-3}$, and $N_2$ is $1 \times 10^6$ cm$^{-3}$, those values may be adopted to accord to the processing equipment and processing conditions.

Figure 12:
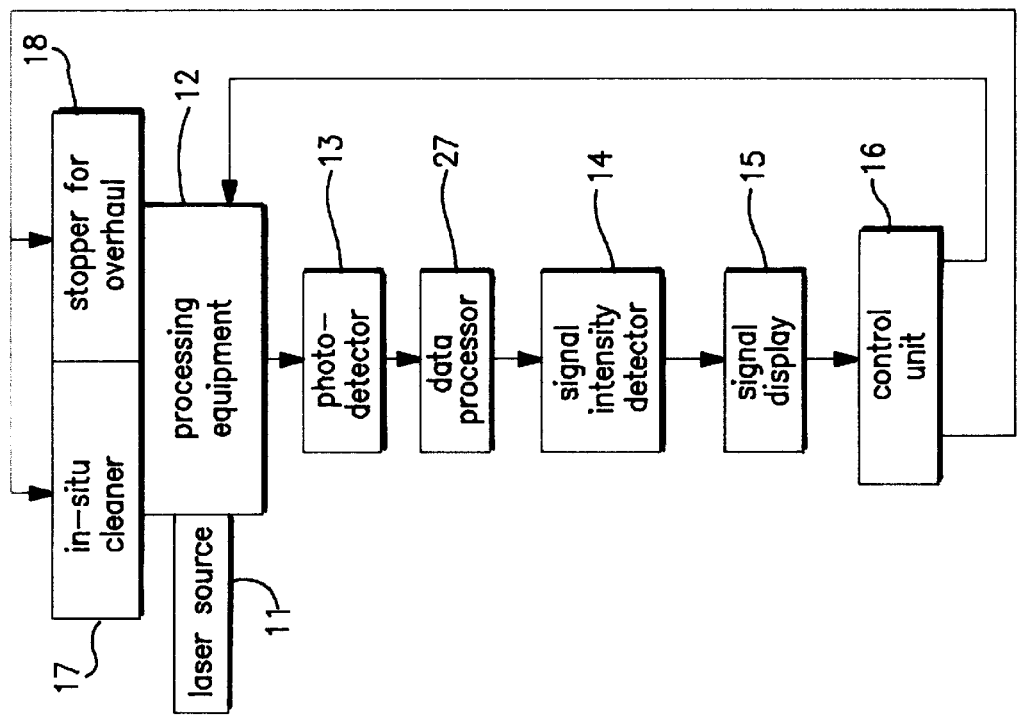
FIG. 12 is yet another structure of a particle monitor in accordance with the present invention.

Further in this embodiment, the signal from the signal intensity judgment device 14 is transmitted to the display 15 and simultaneously to the controller 16. Notwithstanding, it is also possible that as illustrated in FIG. 12, the signal from the signal intensity judgment device 14 is transmitted through the display 15 to the controller 16. In this case, the process engineer reviews the display 15 to operate the controller 16.

In this embodiment, the laser beam is not spatially scanned. It is, however, possible to provide a scanner for scanning spatially laser beam for obtaining two-dimensional and three dimensional distributions of the intensity of the scattered light. Those distributions may be displayed in the display 15 to allow the process engineer to know the generation and distribution of the particles.

THIRD EMBODIMENT

A third embodiment of the present invention will be described, in which a plasma CVD of polysilicon is carried out. It was known that wavelength of the Raman-scattered light is varied depending upon the size of fine particles of silicon. If the silicon particle is 7 nm, the Raman-scattered light is caused at a lower energy than an incident laser beam by an energy of 480 cm$^{-1}$. If the silicon particle is 8 nm, the Raman-scattered light is caused at a lower energy than an incident laser beam by an energy of 485 cm$^{-1}$. If the silicon particle is 10 nm, the Raman-scattered light is caused at a lower energy than an incident laser beam by an energy of 510 cm$^{-1}$. If the silicon particle is 14 nm, the Raman-scattered light is caused at a lower energy than an incident laser beam by an energy of 517 cm$^{-1}$. If the silicon particle is 22 nm, the Raman-scattered light is caused at a lower energy than an incident laser beam by an energy of 520 cm$^1$.

Figure 13:
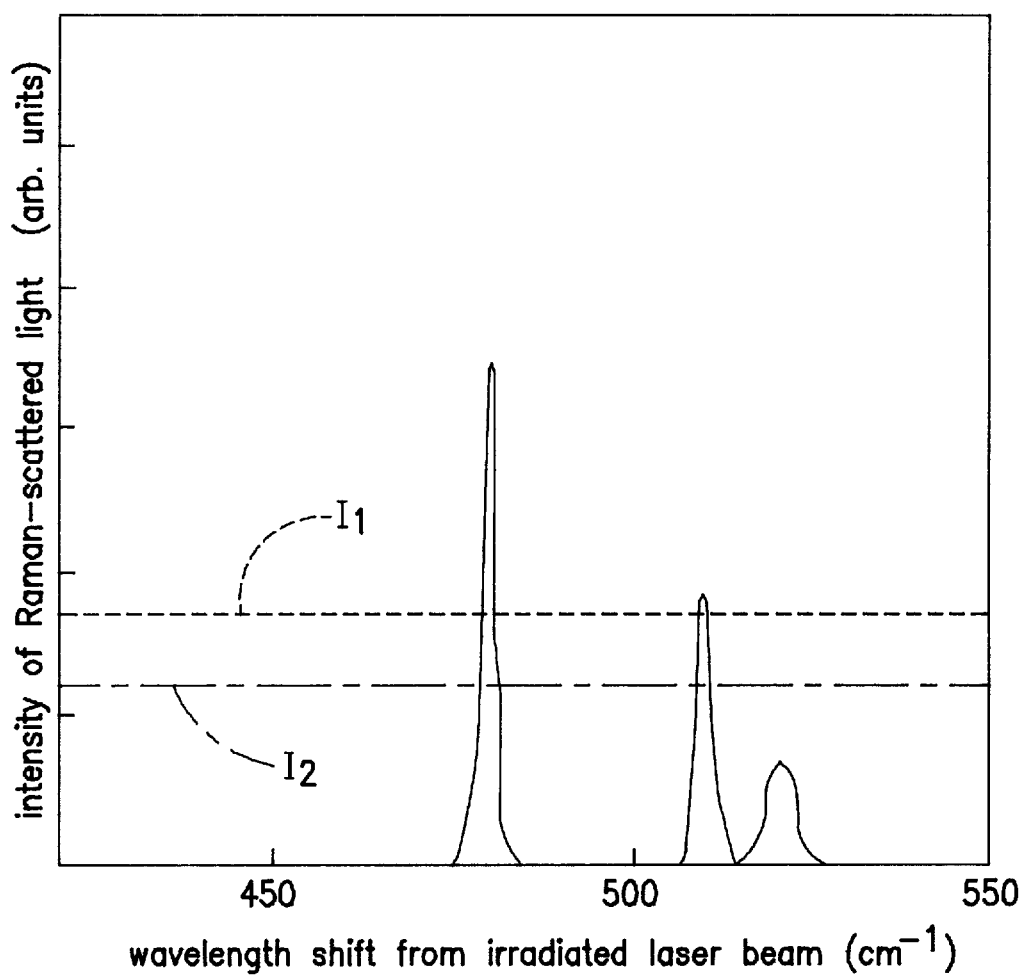
FIG. 13 is a diagram illustrative of a relationship of a Raman-scattered light intensity over shift in wavelength from incident laser beam.

As illustrated in FIG. 13, from the results of the measurement of the intensity to the wavelength of the Raman-scattered light scattered by the polysilicon particles, the intensities $I_1$ and $I_2$ are set. For example, if the intensity at 510 cm$^{-1}$ is smaller than $I_1$, this means no defect due to particle is caused. If however the intensity at 520 cm$^{-1}$ is smaller than $I_2$, this means a large possibility of causing the defect. It is possible to monitor generation of particles by measuring the wavelength and intensity when the Raman-scattered light is caused.

The Raman-scattered light and the Rayleigh scattered light are isolated from each other by a photo-detector 13 comprising a multichannel monochromator and a photomultiplier to measure the intensities. The signals are then transmitted into the signal intensity judgment device 14. In the signal intensity judgment device 14, the intensities $I_1$ and $I_2$ are set for every wavelengths of 510 cm$_{-1}$ and 520 cm$^2$.

If almost no particle has been generated, then almost no scattering of the light from the laser source 11 is caused. As a result, the intensity of the signal transmitted from the photo-detector 13 to the signal intensity judgment device 14 is small. In this case, the intensity of the signal of 510 cm$^{-1}$ is recognized to be smaller than $l_1$ and this signal is then transmitted to the display 14 for display. Also the signal is transmitted to the controller 16 but the controller does not feed-back to the processing equipment 12.

If the signal intensity of 510 cm$^{-1}$ is larger than $l_1$ but the signal intensity of 510 cm$^{-1}$ is smaller than $l_2$, this means particles of 10 nm have been generated. At the same time, the controller 16 issues a stand-by instruction to the in-situ cleaner 17. After the treatment to the wafer in the processing equipment 12 has been finished, then the intended in-situ cleaning is carried out by use of $BCl_3$ gas so that the processing equipment 12 is returned to the normal state.

If both the signal intensities of 510 cm$^{-1}$ and 510 cm$^{-1}$ are larger than $l_2$, the signal is displayed by the display 15. At the same time, the controller 16 issues a stand-by instruction to the processing stopper 18 for external checking to the processing equipment 12. If no abnormal state is confirmed, then the processing equipment will again start operations. If, however, any abnormal state is confirmed, then the overhaul of the processing equipment is made.

The intensity of the scattered light is monitored for comparison to the reference value and from the result of the comparison the controller makes the feed-back to the processor so as to reduce the down time of the processing equipment and reduce the possibility of generation of the particles.

Whereas in this embodiment, the diameter of the particles and number density are set so that $a_1=20$ nm, $a_2=100$ nm $N_1$ is $1\times10^9$ cm$^{-3}$, and $N_2$ is $1\times10^6$ cm$^{-3}$, those values may be adopted to accord to the processor and processing conditions.

Further in this embodiment, the signal from the signal intensity judgment device 14 is transmitted to the display 15 and simultaneously to the controller 16. Notwithstanding, it is also possible that as illustrated in FIG. 12, the signal from the signal intensity judgment device 14 is transmitted through the display 15 to the controller 16. In this case, the process engineer reviews the display 15 to operate the controller 16.

In this embodiment, the laser beam is not spatially scanned. It is, however, possible to provide a scanner for scanning spatially laser beam for obtaining two-dimensional and three dimensional distributions of the intensity of the scattered light. Those distributions may be displayed in the display 15 to allow the process engineer to know the generation and distribution of the particles.

In the foregoing embodiments, the Raman-scattered light and the Rayleigh scattered light are observed. The incident light may be either the continuous laser beam or the pulse laser beam.

FOURTH EMBODIMENT

A fourth embodiment of the present invention will be described, in which a laser source 11 includes an extremely high frequency pulse laser oscillator for emitting a pulse laser of 10 ps and a scanner for spatially scanning the pulse laser. The pulse laser beam is introduced into the processing equipment 12 and scattered by particles. The scattered light is then detected by the photo-detector 13.

The photo-detector 13 has a time-division function at the pulse width for time-dividing the incident laser beam and also has a function of counting the number of pulses. It is possible to confirm the positions of the particles in the processing equipment 12 by measuring the time until the laser beam achieves the photo-detector from the emission thereof.

The data output from the photo-detector 13 is presumed as illustrated in FIG. 15. The amount of the generated pulses may be measured by the number of pulses of the scattered pulse laser beam.

The size of the particle may be found by the intensity of the scattered pulse laser beam on the basis of the intensity of the scattered pulse laser beam. The intensity may be determined by the intensity of the Rayleigh scattered light.

If the incident laser pulse has a pulse width of 10 ps and a speed of the $N_2$ molecules is 500 m/s, then molecules move about 5 micrometers.

If the mass of the particles is increased about 10,000 times, the speed is 1/100 times whereby the distance of movement is about 5 micrometers. This means the spatial resolving power is not less than 5 pm.

As illustrated in FIG. 15, two sets of the reference values are set. Namely, the first set comprises the number of pulses $2\times10^{10}$ cm$^{-3}$ as corresponding to $10^9$ cm$^{-3}$ and pulse intensity $I_1$ as corresponding to the particle size 20 nm. The second set comprises the number of pulses $2\times10^{17}$ cm$^{-3}$ as corresponding to $1\times10^{16}$ cm$^{-3}$ and pulse intensity $I_2$ as corresponding to the particle size 100 nm.

Figure 14:
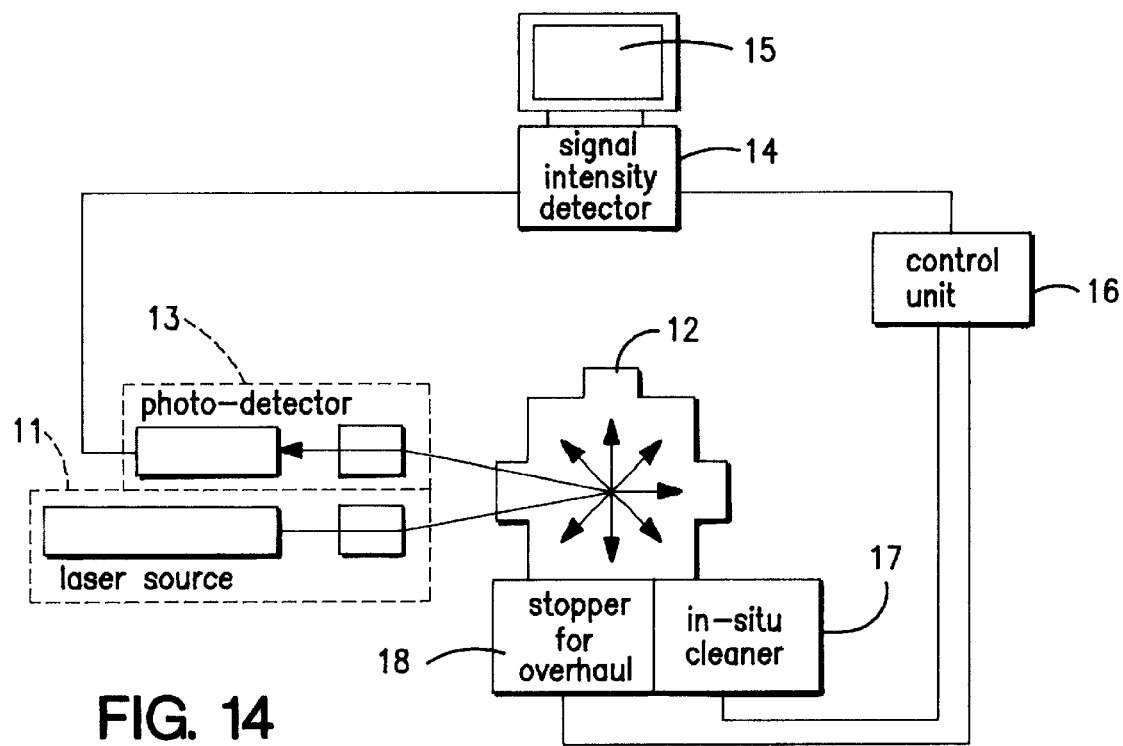
FIG. 14 is a schematic view illustrative of still another structure of a particle monitor in accordance with the present invention.

With reference to FIG. 14, if the measured intensity and number of pulses of the scattered laser pulse are lower than the first reference value, it is recognized that no defect due to particles may be caused whereby no feed-back control to the processing equipment is made.

If the measured intensity and number of pulses of the scattered laser pulse are higher than the first reference value but lower than the second reference value, then the controller 16 issues a stand-by instruction to the in-situ cleaner 17. After the wafer processing has been finished, then the intended in-situ cleaning is carried out whereby the processing equipment 12 is returned to the normal state.

If the measured intensity and number of pulses of the scattered laser pulse are higher than the first and second reference values, then the controller 16 issues a stand-by instruction to the processing stopper 18 for external checking to the processing equipment 12. If no abnormal state is confirmed, then the processing equipment will again start operations. If, however, any abnormal state is confirmed, then the overhaul of the processing equipment is made.

The intensity of the scattered light is monitored for comparison to the reference value and from the result of the comparison the controller makes the feed-back to the processing equipment so as to reduce the down time of the processing equipment and reduce the possibility of generation of the particles.

Whereas in this embodiment, Rayleigh scattered light are observed, it is possible that Raman-scattered light may be observed.

It is also possible to apply the method of measurements of the diameter of the particles, numerical density, and refractive index by analyzing the polarization. In this case, the data processor 27 is inserted between the photo-detector 13 and the signal intensity judgment device 14. The data processor 27 may be the same as described in the second embodiment.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover by claims any modifications of the present invention which fall within the spirit and scope of the present invention.

What is claimed is:

1. A particle monitor comprising:

a light source for emitting a pulsed laser beam;

a transmitter for transmitting the pulsed laser beam through a space above a wafer in a wafer processing equipment to irradiate particles floating above the wafer;

a set of fixed optical analyzer and a rotatable wavelength plate that is rotated every predetermined number of the laser beam pulses for detecting variations in polarization of light scattered by the particles floating in the space to find in real-time Stokes parameters variable over time which are necessary for presumptions of refractive index of particles, and size and distribution of the particles as well as numerical density of the particles;

a photo-detector for detecting the scattered light or luminance to generate output signals corresponding to the intensity of the scattered light;

a signal intensity judgment device for receiving the output signals from the photo-detector and comparing the output signals to a predetermined reference value already set in the signal intensity judgment device so as to judge whether the intensity of the scattered light is higher or lower than the predetermined reference value; and a display for displaying at least one of (a) intensity of the scattered light and luminance and distributions in intensity thereof and (b) distributions in size and the number of particles.

2. The particle monitor as claimed in claim 1, further comprising a controller for controlling operation of the wafer processing equipment on the basis of the output signals of the signal intensity judgment circuit.

3. The particle monitor as claimed in claim 2, further comprising an in-situ cleaner operable under the control of the controller.

4. The particle monitor as claimed in claim 2, further comprising a processing stopper device operable under control of the controller for stopping the operation of the wafer processing for overhaul of the wafer processing equipment.

5. A particle monitor for semiconductor wafer processing equipment, the monitor comprising:

a light source that directs light through a space in the wafer processing equipment that is above a position of a semiconductor wafer so that the directed light does not impinge on the position;

a photo-detector that detects light scattered from particles floating in said space and that generates an output signal corresponding to the intensity of the scattered light when said light source directs the light through said space;

a signal intensity detector that receives the output signal and compares it to a reference value; and a display for displaying the results of the comparison to the reference value, wherein said light source provides a pulsed laser beam, wherein said photo-detector detects light from the floating particles that is scattered perpendicular to the direction of the pulsed lasers light from said light source and comprises a polarizer for polarizing the pulsed laser light from said light source, and a fixed analyzer and a rotatable quarter wavelength plate through which the scattered light is transmitted, and wherein said signal intensity detector comprises means for determining from the output signal the diameter and numerical density of the particles floating in said space.

6. The monitor of claim 5, wherein said light source provides one of a continuous laser beam and a pulsed laser beam.

7. The monitor of claim 5, wherein said signal intensity detector comprises means for determining from the output signal the diameter and numerical density of the particles.

8. The monitor of claim 5, wherein said signal intensity detector comprises means for determining from the output signal whether the particles that scatter the light are caused by flaking from interior surfaces of the space.

9. The monitor of claim 5, wherein said photo-detector comprises a polarizer for polarizing light from said light source, and a fixed analyzer and a rotatable quarter wavelength plate through which the scattered light is transmitted.

* * * * *